United States Patent [19]
Carr et al.

[11] Patent Number: 4,779,173
[45] Date of Patent: Oct. 18, 1988

[54] ILLUMINATED BRUSH DEVICE

[76] Inventors: Charlie O. Carr, 2100 N. Beachwood Dr. #106, Los Angeles, Calif. 90068; Deborah Haugen, 2337 27th St., Santa Monica, Calif. 90405

[21] Appl. No.: 945,888

[22] Filed: Dec. 24, 1986

[51] Int. Cl.$^4$ .................. F21V 33/00; A46B 17/00
[52] U.S. Cl. ............................. 362/109; 362/32; 15/105; 15/167.1
[58] Field of Search ............ 362/32, 109; 15/159 R, 15/167 R, 167.1, 105; 128/393

[56] References Cited

U.S. PATENT DOCUMENTS

| | | | |
|---|---|---|---|
| 2,397,757 | 4/1946 | Schwedersky | 15/160 |
| 2,525,414 | 10/1950 | Kleinschmidt | 362/32 X |
| 2,688,971 | 9/1954 | Daniels et al. | 15/159 R X |
| 3,261,978 | 7/1966 | Brenman | 15/167 R X |
| 4,231,077 | 10/1980 | Joyce et al. | 362/32 |
| 4,253,212 | 3/1981 | Fujita | 15/167 R |

FOREIGN PATENT DOCUMENTS 469964 12/1928 Fed. Rep. of Germany ...... 362/109

Primary Examiner—Ira S. Lazarus
Assistant Examiner—Peggy Neils
Attorney, Agent, or Firm—Grimes & Battersby

[57] ABSTRACT

A brush device having a head, a handle associated with the head, a light source in the handle, and a source for energizing the light source. The brush device also includes a plurality of plastic filaments each having one end position disposed in the handle and adjacent the light source and the other end position disposed in and through the head so that the light from the light source is transmitted through the plurality of plastic filaments and lights the other end of each filament. There may also be provided a magnification member which directs the beam of light into one end portion of the plurality of plastic filaments, as it intensifies same. There may also be provided a color shield so that the light transmitted therethrough assumes a color which corresponds directly to that of the color shield.

7 Claims, 5 Drawing Sheets

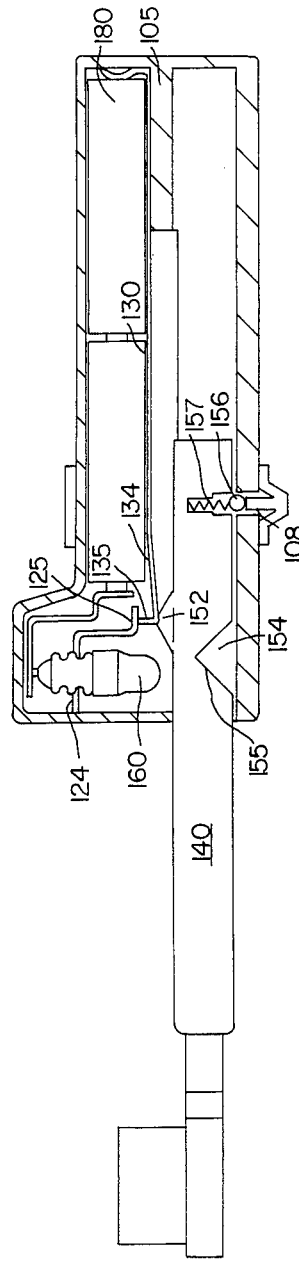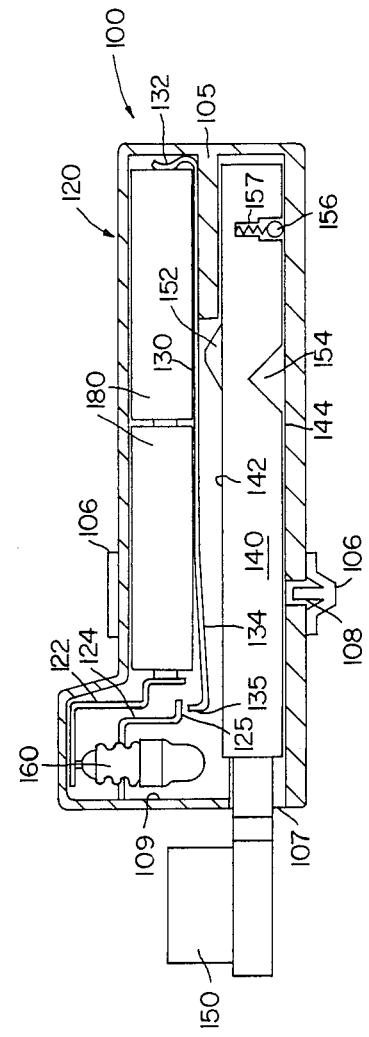

4,779,173

ILLUMINATED BRUSH DEVICE

BACKGROUND OF THE INVENTION

1. Field of the Invention

The present invention relates generally to an illumination device and, more particularly, to a brush device which is capable of becoming illuminated in one or more selected portions thereof by the transmission of light through fiber optic materials.

Heretofore, conventional brushes have suffered from the disadvantage that they provide insufficient lighting in the area to be brushed thereby making it difficult for the user to see clearly the area to be brushed. For example, in conventional implements used for oral hygiene such as a toothbrush, difficulties have been encountered in cleansing all of the teeth in the users mouth due in part, to the inability of the user to have sufficient lighting so as to see all the areas in the mouth. Likewise, in hair brush devices, insufficient lighting has made it difficult to brush and style ones hair.

Attempts have been made to incorporate light in the handle or bristle holding portion of a brush, but heretofore such attempts have produced an implement which is cumbersome, and failed to provide flexibility in the design of the handle of the brush.

2. Description of the Prior Art

A dental cleaning device which attempts to light up the area to be brushed is disclosed in U.S. Pat. No. 3,261,978, which issued on July 19, 1966, in the name of Brenman. This patent discloses a dental cleaning apparatus in which the head portion or bristle holding portion is illuminated. Analogously, U.S. Pat. No. 2,688,971, which issued on Sept. 14, 1954, in the name of Daniels et al., discloses a hairbrush having a light source in the brush head. The brush head, but not the bristles, is directly illuminated by a reflective material disposed in the head to reflect light in the direction of the brush bristles.

U.S. Pat. No. 1,642,187, which issued on Sept. 13, 1927 to Young, Jr., provides a light projector to be used for examining parts of the human body. The light projector includes a rod for transmitting light and a light source such as a bulb. Also provided is the feature of a red disk which may be interposed between the rod and light source in order to project a red ray of light.

Other devices, which can be used to light and illuminate an area have also been disclosed in the prior art. For example, U.S. Pat. No. 2,242,536, which issued on May 20, 1941, in the name of Montgomery, provides for the use of an illuminated handle for work tools, such as a screwdriver.

U.S. Pat. No. 2,261,320, which issued on Nov. 4, 1941, in the name of Williams, provides a combination pencil and flashlight for illuminating the area upon which the pencil is to write. A translucent plug is carried in the casing so that light, which is emitted from a lamp in the casing, is transmitted through the plug and then onto the point of the pencil. Similarly, U.S. Pat. No. 2,344,370, which issued on Mar. 14, 1944, in the name of Shapiro, provides a knitting needle having a body made of plastic. Light is transmitted through the body but emitted only at the tip of the body. Also, U.S. Pat. No. 2,435,650, which issued on Feb. 10, 1948, in the name of Greene, provides a walking stick having an illuminated tip.

More recently, fiber optics have been used to transmit light. For instance, U.S. Pat. No. 3,609,343, which issued on Sept. 28, 1971, in the name of Howlet, provides a decorative light display for use in a fish tank or the like. The light which is transmitted through the optical fibers produces an aesthetically pleasing effect at their light-emitting tips.

U.S. Pat. No. 3,675,005, which issued on July 4, 1972, in the name of Curiel, provides a coiffure decorating apparatus to be worn in the hair, which apparatus employs optic fibers to illuminate the hair. This apparatus is capable of changing the color being transmitted by the optic fibers.

Similarly, U.S. Pat. No. 4,186,425, which issued on Jan. 29, 1980, in the name of Nadimi, is directed to a piece of jewelry having an elongated length of fiber optic material which is adapted to be illuminated, thereby creating an aesthetically pleasing piece of jewelry.

U.S. Pat. No. 3,943,815, which issued on Mar. 16, 1976, in the name of Gilbert, is directed to an illuminated guitar. Specifically, the ends of fiber optic materials are disposed adjacent the fret markers on the neck of the guitar and, when said ends are illuminated, the area proximate the frets is also illuminated.

U.S. Pat. No. 4,302,797, which issued on Nov. 24, 1981, in the name of Cooper, is directed to a hand tool which is adapted to illuminate a workpiece at the point of application of the tool, by a light which is transmitted through one or more optic fibers disposed within the tool.

SUMMARY OF THE INVENTION

Against the foregoing background, it is a primary object of the present invention to provide an illuminating device having plastic filaments which act as bristles of a brush.

It is still another object of the present invention to provide a brush device having plastic filaments which provide a desired color display.

It is still a further object of the present invention to provide such a brush device having plastic filaments, which device includes a magnification means for intensifying the resulting illumination.

It is yet a further object of the present invention to provide a brush device having plastic filaments which act as bristles, with the filaments providing a desired magnified, color light.

It is still yet a further object of the present invention to provide a brush device having an extendable handle and which brush device may have plastic filaments which act as bristles and may provide a desired magnified, color light.

To the accomplishments of the foregoing objects and advantages, the present invention includes an illuminating device comprising a housing and light producing means disposed in the housing. There is also provided a plurality of plastic filaments disposed in the housing. Each of the plurality of plastic filaments has one end portion disposed proximate the light producing means and has the other end portion extending through the housing. When the light producing means is energized, light is transmitted through the plurality of plastic filaments so that the other end portion of each of the plastic filaments is illuminated.

In an alternate embodiment of the present invention, there is provided a brush device comprising a head, a handle associated with the head, and a light producing means disposed in the handle. There is also provided a plurality of plastic filaments each having one end portion disposed in the handle and adjacent the light producing means and having the other end portion disposed through the head. When the light producing means is energized, light is transmitted through the plurality of plastic filaments so as to illuminate the other end portion of each of the plastic filaments.

There may also be provided magnification means disposed within the housing between the light producing means and the one end portion of each of the plastic filaments proximate the light producing means. As light is produced by said light producing means, it is concentrated and directed towards the one end portion of the plastic filaments disposed proximate the light producing means so that the other end portion which extends through the housing, is illuminated.

There may also be provided means for extending the handle so that in the initial position the handle is closed or compact thereby making the brush easier to store and in the second or operative position the handle is opened.

These and other objects will become apparent from the following detailed description.

BRIEF DESCRIPTION OF THE DRAWINGS

The foregoing and still other objects and advantages of the present invention will be more apparent from the following detailed explanation of the preferred embodiments of th invention in connection with the accompanying drawings wherein:

FIGS. 6A and 6B are perspective views of a hairbrush in accordance with the present invention with a portion of the handle cut away to expose the interior elements; and FIG. 6A is a plan view of a toothbrush in accordance with the present invention in which the toothbrush has an extendable handle shown in the closed or non-extended position;

FIG. 6B is a plan view of the toothbrush of FIG. 6A with the handle in the opened or extended position.

DESCRIPTION OF THE PREFERRED EMBODIMENTS

Figure 1:
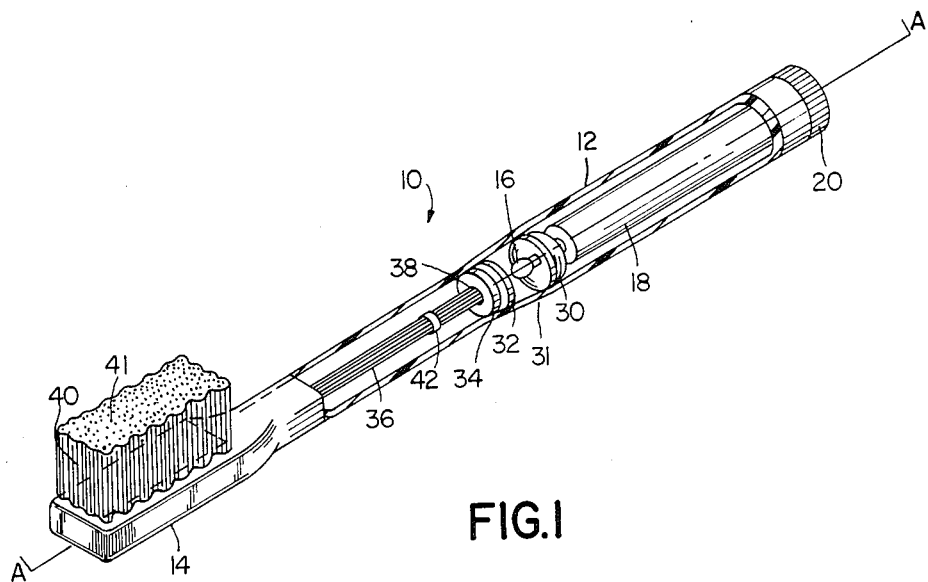
FIG. 1 is perspective view of a toothbrush in accordance with the present invention with a portion of the handle cut away to expose the interior elements.
Figure 2:
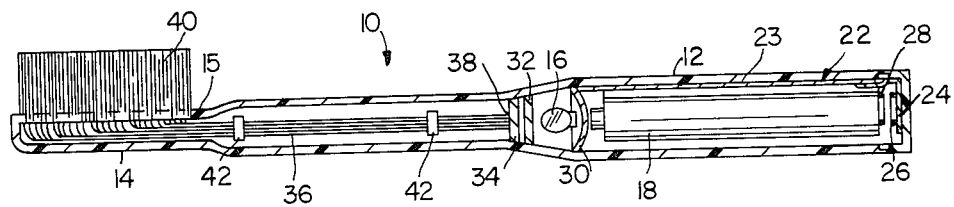
FIG. 2 is a sectional view of the toothbrush of FIG. 1 taken along line A—A of FIG. 1.

Referring now to the drawings and, more particularly, to FIGS. 1 and 2, there is shown a toothbrush, generally represented by reference numeral 10. Toothbrush 10 includes an elongated, stepped handle 12 and a head 14, each of which has a hollow interior. The handle 12 and the head 14, which comprise the housing, can be an integral construction or, alternatively, the handle can be removably mounted to the head. It is preferred that the handle 12 be axially aligned with the head 14, however, the handle can be offset with respect to the head In the interior of the handle 12, there is disposed a light producing means. The light producing means includes a light source 16 and a power supply 18. In a preferred embodiment, the light source 16 is a light bulb, however, other conventional means may be used. The power supply 18, preferably, is a battery, but again other conventional means may be used.

Mounted to the exterior of handle 12 is a means to activate the power circuit (described below) from the light source 16 to the power source 18, such as a switch 20. Switch 20 may be activated by manual rotation in a clockwise or counterclockwise direction, or alternatively, it may be activated by depressing it in the direction of the power supply 18.

Referring to FIG. 2, disposed in the interior of handle 12 is a metal strip 22 which is used to connect or transfer power from the power source or battery 18 to the light source or light bulb 16. Metal strip 22 basically has a U shape configuration. Specifically, metal strip 22 includes a concave end 30 with a center opening (not shown), which end is positioned between the filament portion of the light source 16 and the power source 18, and contacts the interior walls of handle 12. It is preferable in this embodiment that the light source 16 is positioned through the center opening of concave end 30 so as to contact power source 18. Metal strip 22 also includes a center portion 23 extending along the inner wall of handle 12, and a rear end 24. The rear end 24 has fixed to it a contact plate 26. By the movement of switch 20, the contact plate 26 is urged into contact with portion 28 of battery 18, thereby completing the circuit so as to energize the light source 16.

Concave end 30 has a face 31 opposite the light supply 16. Face 31 is a reflecting surface so that when the light supply 16 is illuminated, the light produced therefrom is reflected and directed in the direction of the head 14. It is appreciated that separate reflector means may be provided adjacent the concave end 30 of the metal strip 22 to serve the function of face 31. Although reflecting face 31, preferably, is concave, it may assume other shapes, provided it directs the light rays from the light source 16 towards the head 14. As stated before, the perimeter of concave end 30, and therefore face 31, abuts the inner walls of handle 12, so that in the embodiment shown in FIGS. 1 and 2 the light emanating from the light source 16 is prevented from traveling towards the rear end 24 of handle 12.

After the light, emanating from the light source 16 is reflected off face 31 in the direction of the head 14, it passes through a color shield 32. Color shield 32 causes the light to assume the color of the color shield. Color shield 32 may be a solid color or, alternatively, may assume a variation of colors.

After the light passes through the color shield 32, it then reaches magnification means 34 which intensifies the radiance of the light. Specifically, magnification means 34 concentrates and directs substantially all of the beams of light towards a plurality of plastic filaments 36 so that substantially all of the light is absorbed by and transmitted through the plurality of plastic filaments.

Each of the plurality of plastic filaments of plastic strands 36, has a first end portion 38 disposed within handle 12 and head 14 and abutting magnification means 34. Each plastic filament has a second end portion 40 which pierces through surfaoe 15 of head 14. Preferably, surface 15 has a plurality of tiny apertures (not shown), and the number of apertures corresponds to the number of the plurality of plastic filaments 36.

Each of the individual plastic filaments which comprise the plurality of plastic filaments 36 are preferably of a substantially equal length so that the tips of each of their second end portions 40 forms a generally planar surface. The plurality of plastic filaments may include one or more bands 42 to fix the individual plastic filaments relative to each other.

The plastic filaments employed in the present invention are of the type which transmit light. In a preferred embodiment, the plastic filaments employed are fiber optic strands which transmit light in an efficient and precise manner. The light enters through first end portion 38, is transmitted through the plurality of plastic filaments 36 in an efficient and rapid manner to second end portion 40. Since the light has passed through color corresponding to that of the color shield. It should be understood the illuminated part of second end portion 40 may include all or any portion of the plurality of plastic filaments which have pierced surface 15 of head 14 or the illuminated part of second end portions 40 may simply be the tip 41 of each filament 36.

It should also be understood the second end portions 40 also act as bristles for a toothbrush. In the preferred embodiment, each bristle is a second end portion 40, however, the present invention contemplates a brush having only a portion of the bristles consisting of illuminated end portions 40. Thus the second portions 40 serve both as bristles, as well as means for lighting the mouth during brushing.

It is understood that the relationship of switch 20 to handle 12 shown in FIGS. 1 and 2 is merely illustrative of a preferred relationship and is not intended to limit the means for activating the circuit and energizing the light supply 16. As such, it is also understood that the switch 20 can be activated in other conventional ways.

Figure 3:
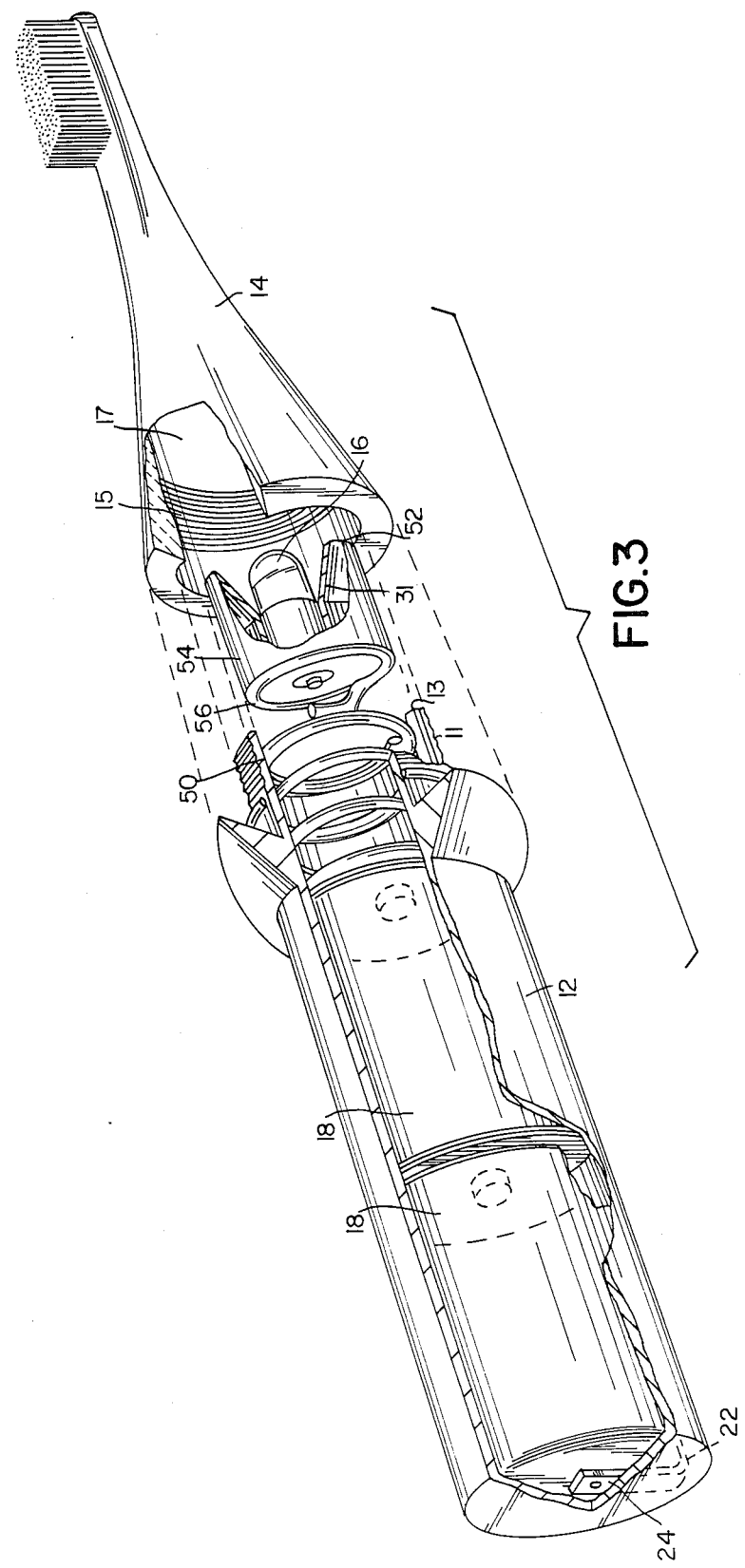
FIG. 3 is another perspective view of a toothbrush in accordance with the present invention with a portion of the handle cut away to expose alternative interior element componentry.

In alternative embodiment shown in FIG. 3, the power supply 18 has two batteries axially aligned. Metal strip 22 has an L shape with rear end 24 contacting the end of one battery when the switch (not shown) is activated, and having the remainder of the strip positioned parallel to the placement of the battery and along the interior of handle 12, terminating before edge 13 of the handle. In this embodiment, handle 12 has a threaded sleeve portion 11 which engages the thread receiving portion 15 of head 14. Within. the threaded sleeve portion 11, there is removable positioned coil spring 50.

Light source 16 is positioned in a reflector 52 having a reflecting surface 31. Reflector 52 is fitted into a plug 54 which is constructed so to snuggly fit within said handle 12 and project into said head 14. Plug 54 is made of a dark plastic so as to assure that light from light source 16 will not be transmitted towards handle 12. Reflecting surface 31 of reflector 52 acts to reflect light in the direction of head 14.

Adjacent plug 54 on the side opposite the light source 16 is a metallic ring 56. Ring 56 is positioned so as to contact coil spring 50 when the threaded sleeve portion 11 of handle 12 engages tightly the threaded receiving portion 15 of head 14.

Reflecting face 31 can be fabricated from any commercially acceptable material which is used to reflect light. Thus, for illustrative purposed only, face 31 may be fabricated from a shiny metallic substance, or a reflective glass material, or it may simply be treated with a reflective paint. In the embodiment, the reflecting surface 16 of reflector 52 provide sufficient light so as to light up the interior 17 of the shaft of head 14. However, to further enhance the lighting, a plurality of plastic filament or plastic straions, as shown in FIGS. 1 and 2, may also be used.

Figure 4:
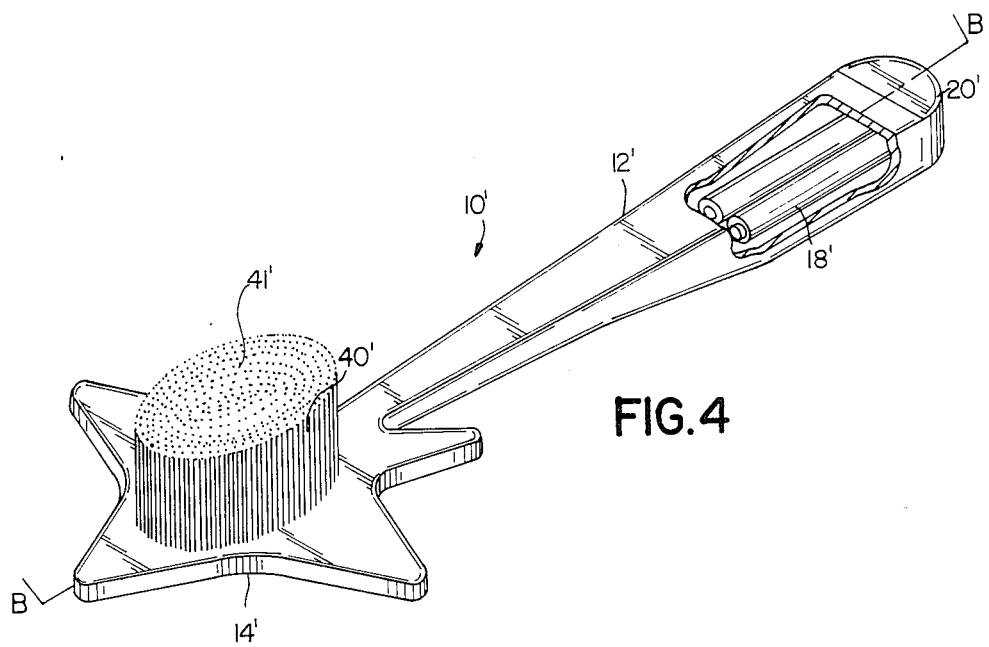
FIG. 4 is a perspective view of a hairbrush in accordance with the present invention with a portion of the handle cut away to expose the interior elements.
Figure 5:
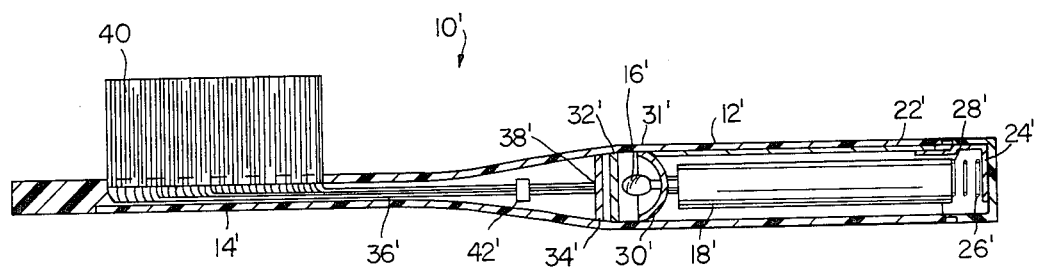
FIG. 5 is a sectional view of the hairbrush of FIG. 4 taken along line B—B.

FIGS. 4 and 5 illustrates the present invention as applied to a hairbrush with like parts with respect to FIGS. 1 and 2 designated by like (primed) reference numerals. The hairbrush 10' includes a housing comprising a handle 12' and a head portion 14'. In this embodiment, it is preferable that the power supply 18' includes two batteries, such as two triple A batteries. The light bulb 16' may be energized in a manner similar to that for the toothbrush 10 of FIGS. 1 and 2. Specifically, there is provided in sequence reflecting face 31', color shield 32', and magnification means 34' and the plurality of plastic filaments 36' so that the second end portions 40', or alternatively the tips 41' of the plurality of plastic filaments 36', provide magnified light corresponding in color to that of the color shield and also the second end portions act as brush bristles.

FIG. 6A shows an embodiment of the present invention in which the handle 120 of the toothbrush 100 is extendable. In this embodiment, the toothbrush, 100 has a housing 105 with a molded rubber collar 106 having a pin portion 108.

In the upper portion of housing 105, there is located a light source, such as light bulb 160, and a power source, such as a pair of batteries 180. A first metal strip 122 is secured to an interior surface of the upper portion of housing 105, and is positioned so as to contact light bulb 160 and power source 180 and thereby connect them together. A second metal strip 124, which is connected to an interior side wall 109 of the upper portion of housing 105, has a ring portion through which the light bulb 160 is secured and a free end 125. A third metal strip 130 is positioned in the upper portion of housing 105. The thick metal strip 130 has a first end 132 which is adapted to contact one of the pair of batteries when the batteries are inserted into the handle 120, an elongated portion 134, and a second end portion 135. It should be understood that batteries commonly know as AAA batteries or triple A batteries should be used because of their small size. As shown in the closed embodiment of FIG. 6A, a rod 140 is located in the lower portion of the housing 105 and extends slightly through aperture 107 of the housing. The portion of the rod 140 extending through the housing has connected to it head 150 of the toothbrush 100. Rod 140 has a triangular abutment 152 on its upper exterior surface 142. In the interior of lower surface 144 of the rod 140, there is provided a triangular member 154. Through the lower surface 144 there is a hole in which there is housed a ball 156 and spring 157 mechanism. The spring 157 is biased so as to exert force on the ball 156. As shown in this FIG. 6A, the spring 157 forces the ball 156 against the interior of the housing 105 so as to form a friction contact with the housing thereby preventing the rod 14 from sliding.

Referring to FIG. 6B, the rod 140 has been released or extended by manually pulling rod 140 out of housing 105. Rod 140 is extended until it reaches the position where the spring 157 forces ball 156 into the hole in housing 105 where pin portion 108 is located. At this position, triangular abutment 152 contacts portion 134 and second end portion 135 of the third metal strip 130 and drives the second end portion into contact with the free end 125 of the second metal strip 124. When free end 125 contacts the second end portion 135 a circuit between the light bulb 160 and the pair of batteries 180 is complete so that the light bulb is energized or lighted. When the rod 140 is in this position, the light from light bulb 160 is directed towards panel 155 of triangular member 154. Triangular member 154 has been painted white so as to reflect the light towards the head 150. For the light from light source 160 to reflect off panel 155, rod 140 must be transparent. Specifically, rod 140 must be made of a transparent acrylic plastic material. Thus, it is important that triangular abutment 152, triangular member 154 and the hole for ball 156 and spring 157 be in a certain relationship with respect to one another, so that when ball 156 contacts pin portion 108, triangular abutment 152 has contacted and sent second end portion 135 into free end 125, and triangular member 154 is located such that panel 155 directs, in an optimum fashion, the light from light bulb 160 towards head 150. It should be understood that to return rod 140 to the closed position shown in FIG. 6A, collar 106 is activated such that pin portion 108 drives ball 156 upwards against spring 157 until the ball is in the rod so that the rod can slide back into housing 105.

Figure 7:
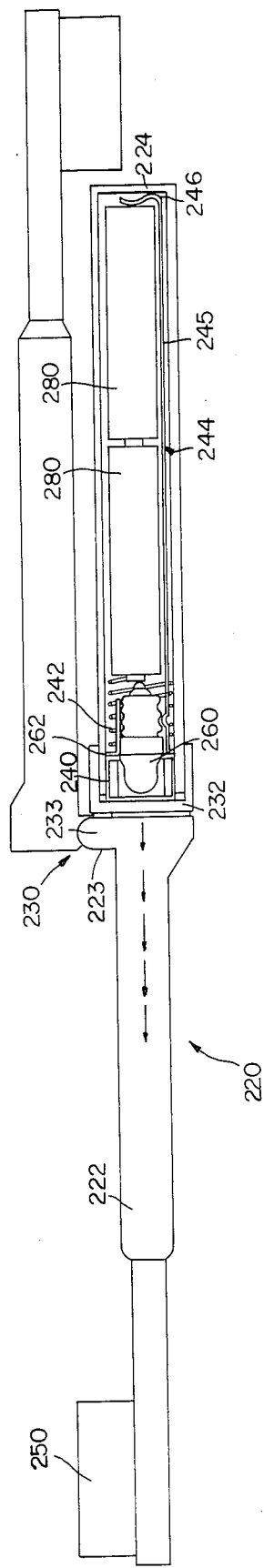
FIG. 7 is a plan view of a toothbrush in accordance with the present invention in which the toothbrush has a rotatable handle.

In the extendable handle embodiment shown in FIG. 7, handle 220 is composed of a first portion 222 and a second portion 224 which are connected together by hinge means 230. Hinge means 230 includes a cap 232 which is threaded onto the exterior of second portion 224. Cap 232 has a flange (not shown) and a pin 233 which engages the flanged portion 223 of first portion 222 so as to provide for the pivoting of the first portion with respect to the second portion between the closed position, shown in dotted lines in FIG. 5, to the open position, shown in solid lines in FIG. 7.

The first portion 222 is made of a transparent material, such as acrylic plastic. Second end portion 224 is made of a non-transparent material. Cap 232 is made of clear acrylic plastic.

In the interior of second portion 224, there is provided a molded collar 240. The molded collar is positioned at the end of second portion 224 adjacent first portion 222. In second portion 224, there is also provided a spring 242, metal strip 244 and space to house a light source, such as light bulb 260, and a power source, such as a pair of batteries 280. Spring 242 is adapted to fit about light bulb 260 and is located between collar 224 and the power source or pair of batteries 280. The metal strip 244 has an elongated portion 245 and a serrated end 246. The end 246 is positioned between the power source 280 and the end of second portion 224 opposite first portion 222, and contacts the power source when a pair of triple A batteries are in place in the second portion of the handle 220. Triple A batteries are used as in the embodiment of FIGS. 6A and 6B, because of their size.

The elongated portion 245 is positioned below the light source 260 and power source 280 and has a free end which extends to collar 262 of the light bulb 260. The spring 242 acts to bias the light bulb 260 away from the power source 280 so that collar 262 strikes molded collar 240. However, when cap 232 is tightened, collar 240 overcomes the biasing action of spring 242 and forces collar 262 and light bulb 260 back against one of the pair of batteries 280 so as to energize or light the light bulb 260.

As in the embodiment of FIG. 3, the light bulb 260 has sufficient light so as to light the shaft or first portion 222 of handle 220. However, to provide enhanced light the first portion 222 has contained therein a plurality of optic fibers (like those shown in FIGS. 1 and 2) which receive the light from light bulb 260 and conveys the light to head portion 250.

Having thus described the invention with particular reference to the preferred forms thereof, it will be obvious that various changes and modifications may be made therein without departing from the spirit and scope of the invention as defined by the appended claims.

Wherefore, we claim:

1. A brush device comprising:
   a head having a hollow interior and having a threaded sleeve portion;
   a handle having a hollow interior and having a threaded sleeve portion adapted to the connected to said hollow sleeve portion of said head to connect together said handle and said head;
   reflector means having a plug which is adapted to snugly fit in said handle and project into said head and having a reflector connected to said plug; said reflector having reflector surface for reflecting light in the direction of the end of said head opposite said handle, said plug being made of a dark material;
   light producing means positioned in said reflector;
   energizing means for energizing said light producing means when said handle and said head are connected together; and
   a plurality of brush bristles disposed in said head, each of said plurality of bristles being a plastic filament having one end disposed proximate said light producing means and having an opposite end extending through said head,
   wherein light is transmitted through said plurality of brush bristles and illuminates said opposite end of each of said plurality of brush bristles when said light producing means is energized by said energizing means, and
   wherein said plug prevents light from said light producing means from reflecting towards said handle.

2. The device of claim 1, wherein said head is mounted to said handle.

3. The device of claim 1, wherein said light producing means is a light bulb.

4. The device of claim 1, wherein said opposite end of each of said plurality of brush bristles extends through a plurality of apertures in a surface of said head.

5. The device according to claim 1, wherein said brush device is a hairbrush.

6. The device of claim 1, wherein said brush device is a toothbrush.

7. The device of claim 1, wherein said reflector means is disposed in said body proximate said light producing means.

* * * * *